(12) United States Patent
Chen et al.

(10) Patent No.: US 7,838,073 B2
(45) Date of Patent: Nov. 23, 2010

(54) TANTALUM AMIDE COMPLEXES FOR DEPOSITING TANTALUM-CONTAINING FILMS, AND METHOD OF MAKING SAME

(75) Inventors: Tianniu Chen, Rocky Hill, CT (US); Chongying Xu, New Milford, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 12/773,650

(22) Filed: May 4, 2010

(65) Prior Publication Data

US 2010/0215842 A1 Aug. 26, 2010

Related U.S. Application Data

(63) Continuation of application No. 12/119,463, filed on May 12, 2008, now Pat. No. 7,709,384, which is a continuation of application No. 11/625,918, filed on Jan. 23, 2007, now Pat. No. 7,371,878, which is a continuation of application No. 11/224,588, filed on Sep. 12, 2005, now Pat. No. 7,198,815, which is a continuation of application No. 10/684,545, filed on Oct. 14, 2003, now Pat. No. 6,960,675.

(51) Int. Cl.
*C23C 16/00* (2006.01)
*C07F 9/00* (2006.01)

(52) U.S. Cl. .............................. 427/255.395; 427/96.8; 427/126.1; 427/255.394; 556/42

(58) Field of Classification Search ................ 427/96.8, 427/126.1, 255.394, 255.395; 556/42
See application file for complete search history.

(56) References Cited

U.S. PATENT DOCUMENTS

| | | | |
|---|---|---|---|
| 3,843,536 A | 10/1974 | Johnston et al. | |
| 3,978,272 A | 8/1976 | Donley | |
| 4,147,556 A | 4/1979 | Donley | |
| 4,401,474 A | 8/1983 | Donley | |
| 4,510,222 A | 4/1985 | Okunaka et al. | |
| 4,643,913 A | 2/1987 | Okunaka et al. | |
| 4,933,317 A | 6/1990 | Johnson, Jr. et al. | |
| 4,993,361 A | 2/1991 | Unvala | |
| 5,045,348 A | 9/1991 | Brierley et al. | |
| 5,130,172 A | 7/1992 | Hicks et al. | |
| 5,204,314 A | 4/1993 | Kirlin et al. | |
| 5,225,561 A | 7/1993 | Kirlin et al. | |
| 5,266,355 A | 11/1993 | Wernberg et al. | |
| 5,280,012 A | 1/1994 | Kirlin et al. | |
| 5,376,409 A | 12/1994 | Kaloyeros et al. | |
| 5,453,494 A | 9/1995 | Kirlin et al. | |
| 5,504,195 A | 4/1996 | Leedham et al. | |
| 5,536,323 A | 7/1996 | Kirlin et al. | |
| 5,555,154 A | 9/1996 | Uchikawa et al. | |
| 5,656,329 A | 8/1997 | Hampden-Smith et al. | |
| 5,677,002 A | 10/1997 | Kirlin et al. | |
| 5,679,815 A | 10/1997 | Kirlin et al. | |
| 5,711,816 A | 1/1998 | Kirlin et al. | |
| 5,820,664 A | 10/1998 | Gardiner et al. | |
| 5,840,897 A | 11/1998 | Kirlin et al. | |
| 5,876,503 A | 3/1999 | Roeder et al. | |
| 5,894,064 A | 4/1999 | Hampden-Smith et al. | |
| 5,916,359 A | 6/1999 | Baum et al. | |
| 5,935,283 A | 8/1999 | Sweeney et al. | |
| 6,006,582 A | 12/1999 | Bhandari et al. | |
| 6,015,917 A | 1/2000 | Bhandari et al. | |
| 6,018,065 A | 1/2000 | Baum et al. | |
| 6,077,571 A | 6/2000 | Kaloyeros et al. | |
| 6,110,529 A | 8/2000 | Gardiner et al. | |
| 6,126,996 A | 10/2000 | Kirlin et al. | |
| 6,143,191 A | 11/2000 | Baum et al. | |
| 6,214,105 B1 | 4/2001 | Hintermaier et al. | |
| 6,218,518 B1 | 4/2001 | Baum et al. | |
| 6,265,222 B1 | 7/2001 | DiMeo et al. | |
| 6,273,951 B1 | 8/2001 | Vaartstra | |
| 6,277,436 B1 | 8/2001 | Stauf et al. | |
| 6,284,654 B1 | 9/2001 | Roeder et al. | |
| 6,340,769 B1 | 1/2002 | Baum et al. | |
| 6,344,079 B1 | 2/2002 | Baum | |
| 6,379,748 B1 | 4/2002 | Bhandari et al. | |
| 6,399,208 B1 | 6/2002 | Baum et al. | |

(Continued)

FOREIGN PATENT DOCUMENTS

DE 43 32 890 A1 3/1994

(Continued)

OTHER PUBLICATIONS

Allen, Frank. H. et al., "Tables of Bond Lengths Determined by X-ray and Neutron Diffraction", "J. Chem. Soc. Perkin Tran. II", Feb. 1987, pp. S1-S19.

(Continued)

*Primary Examiner*—Porfirio Nazario Gonzalez
(74) *Attorney, Agent, or Firm*—Steven J. Hultquist; Intellectual Property/Technology Law; Maggie Chappuis

(57) ABSTRACT

Tantalum precursors useful in depositing tantalum nitride or tantalum oxides materials on substrates, by processes such as chemical vapor deposition and atomic layer deposition. The precursors are useful in forming tantalum-based diffusion barrier layers on microelectronic device structures featuring copper metallization and/or ferroelectric thin films.

20 Claims, 8 Drawing Sheets

U.S. PATENT DOCUMENTS

| | | | |
|---|---|---|---|
| 6,444,264 | B2 | 9/2002 | Hintermaier et al. |
| 6,511,936 | B1 | 1/2003 | Theopold et al. |
| 6,552,209 | B1 | 4/2003 | Lei et al. |
| 6,593,484 | B2 | 7/2003 | Yasuhara et al. |
| 6,821,921 | B2 | 11/2004 | Theopold et al. |
| 6,960,675 | B2 | 11/2005 | Chen et al. |
| 6,989,457 | B2 | 1/2006 | Kamepalli et al. |
| 7,034,169 | B1 | 4/2006 | Norman |
| 7,094,284 | B2 | 8/2006 | Baum et al. |
| 7,112,690 | B2 | 9/2006 | Chi et al. |
| 7,198,815 | B2 | 4/2007 | Chen et al. |
| 7,205,422 | B2 | 4/2007 | Norman |
| 7,323,581 | B1 | 1/2008 | Gardiner et al. |
| 7,329,768 | B2 | 2/2008 | Kamepalli et al. |
| 7,371,878 | B2 | 5/2008 | Chen et al. |
| 2002/0000175 | A1 | 1/2002 | Hintermaier et al. |
| 2006/0292303 | A1 | 12/2006 | Millward et al. |
| 2007/0117385 | A1 | 5/2007 | Chen et al. |
| 2009/0004858 | A1 | 1/2009 | Chen et al. |
| 2009/0032952 | A1 | 2/2009 | Chen et al. |
| 2009/0087561 | A1 | 4/2009 | Chen et al. |

FOREIGN PATENT DOCUMENTS

| | | |
|---|---|---|
| JP | 59-168678 A | 9/1984 |
| JP | H07-263431 A | 10/1995 |
| JP | 08-074055 A | 3/1996 |
| WO | 9304072 A1 | 3/1993 |
| WO | 9608587 A1 | 3/1996 |
| WO | 9640690 A1 | 12/1996 |
| WO | 9900530 A1 | 1/1999 |
| WO | 9927030 A1 | 6/1999 |

OTHER PUBLICATIONS

Antinolo, A. et al., "Bonding Interactions Between Three Adjacent Hydrogen Ligands. Preparation and Spectroscopic Properties of the Tantalum..", 1988, pp. 1210-1212, vol. 17.

Antinolo, A. et al., "Exchange Coupling in Niobocene Trihydrides, Nb(C5H3RR')2H3, and Their Adducts with Copper Triad Cations...", "Inorganic Chemistry", 1996, pp. 7873-7881, vol. 35, No. 26.

Bilodeau, S. et al., "Dielectric properties of Very Thin Films of Ba.7Sr.3TiO3", "Proceedings of the Int. Conf. on Solid State Devices and Materials", 1997, pp. 797-799.

Bilodeau, S. et al., "Process and Thin Film Characteristics of TaN Deposited by MOCVD", "Proceedings of the Int. Conf. on Solid State Devices and Materials", 2001, pp. 609-612, Publisher: Materials Research Society.

Bradley, Donald C., et al., "Metallo-organic compounds containing metal-nitrogen bonds: Part I, some dialkyamino derivatives of titanium and...", "J. Chem. Soc.", Oct. 1960, pp. 3857-3861.

Bradley, Donald C., et al., "Metallo-organic compounds containing metal-nitrogen bonds: Part III, Dialkylamino compounds of tantalum", "Canadian J. Chem.", Jul. 12, 1962, pp. 1355-1360, vol. 40, No. 7.

Castro, A. et al., "Mixed-dicyclopentadienyl niobium and tantalum complexes: synthesis and reactivity. X-ray molecular structures...", "Journal of Organometallic Chemistry", 1996, pp. 37-46, vol. 518, No. 1-2.

Chen, C. et al., "Synthesis and catalytic properties of oxalic amidinato complexes", "J. Chem. Society, Dalton Trans.", May 15, 2001, pp. 1761-1767, Publisher: The Royal Society of Chemistry.

Chisholm, M. et al., "Chloro(dimethylamido) Compounds of Tantalum(V): Preparations, Properties, and Structures of [Ta(NMe2)3Cl2]2...", "Inorganic Chemistry", 1981, pp. 1859-1866, vol. 20.

Chiu, Hsin-Tien, et al., "Deposition of tantalum nitride thin films from ethylimidotantalum complex", "J. Mater. Sci. Lett.", Jan. 1992, pp. 96-98, vol. 11, No. 2.

Chiu, H. et al., "Deposition of tanatlum nitride thin films from ethylimidotanatlum", "Journal of Materials Science Letters ll", 1992, pp. 96-98.

Tsai, M.H., et al., "Metal-organic chemical vapor deposition of tantalum nitride barrier layers for ULSI applications", "Thin Solid Films", Dec. 1, 1995, pp. 531-536, vol. 270, No. 1-2.

Engbrecht, E. et al., "Chemical vapor deposition growth and properties of TaCxNy", "Thin Solid Films", 2002, pp. 145-150, vol. 418.

Fan, M. et al., "Peculiar Hydride-Silyl Interactions in Group 5 Bent Metallocene Complexes, Studied by ab Initio Calculations", "Organometallics", 1998, pp. 1092-1100, vol. 17, No. 6.

Fix, Renaud, et al., "Chemical vapor deposition of vanadium, niobium, and tantalum nitride thin films", "Chem. Mater.", May 1993, pp. 614-619, vol. 5, No. 5.

Foust, D. et al., "Photodegradation studies on di-n5-cyclopentadienyldimethyl-tantalum and some deuterated analogs", "Journal of Organometallic Chemistry", 1982, pp. 47-55, vol. 226, No. 1.

Gade, L. et al., "New transition metal imido chemistry with diamidodonor ligands", "Coordination Chemistry Reviews", 2001, pp. 65-97, vol. 216-217.

Gillan, E. et al., "Volatility Studies on Gallium Chalcogenide Cubanes: Thermal Analysis and Determination of Sublimation Enthalpies", "Chem. Mater.", 1997, pp. 796-806, vol. 9, Publisher: American Chemical Society.

Hieber, K., "Structural and electrical properties of Ta and Ta nitrides deposited by chemical vapour deposition", "Thin Solid Films", Nov. 1974, pp. 157-164, vol. 24, No. 1.

Holloway, Karen, et al., "Tantalum as a diffusion barrier between copper and silicon: Failure mechanism and effect of nitrogen additions", "Journal of Applied Physics", Jun. 1, 1992, pp. 5433-5444, vol. 71, No. 11.

Im, S. et al., "A Study on CVD TaN as a Diffusion Barrier for Cu Interconnects", "Mat. Res. Symp. Proc.", 2000, pp. D671-D676, vol. 612, Publisher: Materials Research Society.

Jiang, Qian, et al., "Synthesis of mono- and bis(silyl) complexes of tantalum", "Organometallics", Oct. 1991, pp. 3648-3655, vol. 10, No. 10.

Jiang, Q. et al., "Thermochemical Aspects of Arene C-H Activation by Tantalum Silyl Complexes: Relative Ta-Si and Ta-C bond enthalpies", "Journal of Organometallic Chemistry", Sep. 1994, pp. 3679-3691, vol. 13, No. 9.

Tsai, M.H., et al., "Metalorganic chemical vapor deposition of tantalum nitride by tertbutylimidotris(diethylamido)tantalum for advanced...", "Appl. Phys. Lett.", Aug. 21, 1995, pp. 1128-1130, vol. 67, No. 8.

Kim, H. et al., "Diffusion Barrier Properties of Transition Metal Thin Fims Grown by Plasma-Enhanced Atomic-Layer Deposition", "J. Vac. Sci. Technology", Jul. 2002, pp. 1321-1327, vol. 20, No. 4.

Kim, H., "Atomic layer deposition of metal and nitride thin films: Current research efforts and applications for semiconductor...", "J. Vac. Sci. Technol.", Nov. 3, 2003, pp. 2231-2260, vol. 21, No. 6.

Kim, H. et al., "Growth of Cubic TaN Thin Films by Plasma-Enhanced Atmic Layer Deposition", "J. Applied Physics", Dec. 15, 2002, pp. 7080-7086, vol. 92, No. 12.

Kingon, A. et al., "Alternative dielectrics to silicon dioxide for memory and logic devices", "Nature", Aug. 31, 2000, pp. 1032-1038, vol. 406.

Kirlin, Peter S., et al., "Growth of High Tc YBaCuO Thin Films by Metalorganic Chemical Vapor Deposition", "SPIE", 1988, pp. 115-127, vol. 1187.

Kirlin, Peter S., et al., "Thin Films of Barium Fluoride Scintillator Deposited by Chemical Vapor Deposition", "Nuclear Instruments and Methods in Physics Research", 1990, pp. 261-294, vol. A, No. 289.

Leblanc, J. et al., "Coordination Chemistry.—Substituted Biscyclopentadienyl Tantale Complexes: Synthesis and Reactivity of Dicholorides...", 1982, pp. 755-757, vol. 295, No. 8.

Lim, S. et al., "A Study on the Development of Chemical Vapor Deposition Precursors. 4. Syntheses and Characterization of New N-Alkoxoy..", "Chem. Mater.", 2002, pp. 1548-1554, vol. 14, Publisher: American Chemical Society.

Nicolet, M., "Diffusion Barriers in Thin Films", "Thin Solid Films", 1978, pp. 415-433, vol. 52, Publisher: Elsevier Sequoia S.A.

Olowolafe, J.O., et al., "Interdiffusions in Cu/reactive-ion-sputtered TiN, Cu/chemical-vapor-deposited TiN, Cu/TaN, and TaN/Cu/TaN thin-film . . .", "Journal of Applied Physics", Nov. 1, 1992, pp. 4099-4103, vol. 72, No. 9.

Park, J. et al., "Plasma-Enhanced Atomic Layer Deposition of Tantalum Nitrides Using Hydrogen Radicals as a Reducing Agent", "Electrochemical and Solid State Letters", Mar. 9, 2001, pp. C17-C19, vol. 4, No. 4.

Park, J. et al., "Plasma-Enhanced Atomic Layer Deposition of TaN Thin Films", "Journal of the Electrochemical Society", Nov. 27, 2001, pp. C28-C32, vol. 1.

Parkin, G. et al., "Alpha- and beta-migratory insertion and elimination processes for alkyl complexes of permethylscandocene and permethylta", "Journal of Molecular Catalysis", 1987, pp. 21-39, vol. 41, No. 1-2.

Pollard, K. et al., "Chemical Vapor Deposition of Tantalum Oxide from Tetraethoxo(Beta-diketonato)tantalum(V)Complexes", "Chem. Mater.", Mar. 31, 1999, pp. 1069-1074, vol. 11, Publisher: American Chemical Society.

Pugh, S. et al., "Group 5 Imido Complexes Supported by Diamidopyridine Ligands: Aryloxide, Amide, Benzamidinate, Alkyl, and . . .", "Organometallics", 2001, pp. 3531-3542, vol. 20, Publisher: American Chemical Society.

Richardson, M., et al., "Volatile rare earth chelates of 1,1,1,5,5,5-hexafluoro-2,4-pentanedione and 1,1,1,2,2,3,3,7,7,7-decafluoro-4,6-heptanedi", "Inorganic Chemistry", 1971, pp. 498-504, vol. 10, No. 3.

Riley, P. et al., "Formation of Tantalum 'Tuck-in' Complexes by Activation of Methyl-C-H Bonds in Pentamethylcyclopentadiene Groups . . .", "Organometallics", Aug. 12, 1999, pp. 3579-3583, vol. 18.

Stoll, S. et al., "Selenide and selenolate compounds of indium: a comparative study of In]Se bond-forming reactions", "J.Chem. Soc., Dalton Trans.", 1997, pp. 1315-1321.

Sun, Xin et al., "Properties of reactively sputter-deposited Ta-N thin films", "Thin Solid Films", 1993, pp. 347-351, vol. 236.

Sun, S.C., et al., "Performance of MOCVD tantalum nitride diffusion barrier for copper metallization", "1995 Symp. on VLSI Technol. Digest of Technical Papers", Jun. 1995, pp. 29-30.

Tabuchi, Toshiya, et al., "Application of penta-di-methyl-amino-tantalum to a tantalum source in chemical vapor deposition of tantalum oxide films", "Japanese Journal of Applied Physics", Nov. 1991, pp. L1974-L1977, vol. 30, No. 11B.

Thirupathi, N. et al., "Mono-and Dianionic Guanidinate Ligands", "Organometallics", May 31, 2000, pp. 2573-2579, vol. 19.

Tin, M. et al., "Insertion Routes to Tetrasubstituted Guanidinate Complexes of Ta(V) and Nb(V)", "Inorganic Chemistry", Feb. 18, 1999, pp. 998-1001, vol. 38.

Zhang, Jiming, et al., "Metal organic chemical vapor deposition of LaSrCoO electrodes for ferroelectric capacitors", "6th ISAF Mtg.", Mar. 1994.

Zhao, Jing, "Organometallic chemical vapor deposition of high Tc superconducting films using a volatile, fluorocarbon-based precursor", "Applied Physics Letters", Oct. 31, 1988, pp. 1750-1752, vol. 53, No. 18.

Van Buskirk, Peter C., et al., "MOCVD growth of BaTiO3 in an 8-inch single-wafer CVD reactor", "Proc. ISAF, Eighth Int'l Symp. Appl. Ferroelectrics", Aug. 31-Sep. 2, 1992, vol. 92.

Weimer, A. et al., "Chemical Purification, Chemical Vapor Deposition and Infiltration, and Plasma Enhanced Chemical Vapor Deposition", "Carbide, Nitride, and Boride Materials Synthesis and Processing", 1997, pp. 479-502, 547-601, Publisher: Chapman and Hall.

Williams, P. et al., "The Unusual Thermal Stabilization of MOCVD Precursors by the Dibenzoyl Methanate Group: Liquid Injection MOCVD . . .", "Chemical Vapor Deposition", 2002, pp. 110-116, vol. 8, No. 3.

Winter, Charles H., "Single-source precursors to niobium nitride and tantalum nitride films", "Mat. Res. Soc. Symp. Proc.", 1994, pp. 103-108, vol. 327, No. 1.

Zhang, K., et al., "Metalorganic chemical vapor deposition of Tl2CaBa2Cu2Oy superconducting thin films on sapphire", "Applied Physics Letters", Sep. 18, 1989, pp. 1258-1260, vol. 55, No. 12.

Zhang, Jiming, et al., "Single liquid source plasma-enhanced metalorganic chemical vapor deposition of high quality YBa2Cu3O7-x thin films", "Applied Physics Letters", Dec. 14, 1992, pp. 2884-2886, vol. 61, No. 24.

Zhang, Jiming, et al., "Plasma enhanced metalorganic chemical vapor deposition of conductive oxide electrodes for ferroelectric BaTiO3 capacitor", "Mater. Res. Soc. Symp. Proc.", 1993, pp. 249-254, vol. 310.

Unpublished U.S. Appl. No. 11/949,871, (2007).

Unpublished U.S. Appl. No. 12/790,835, (2010).

TANTALUM AMIDE COMPLEXES FOR DEPOSITING TANTALUM-CONTAINING FILMS, AND METHOD OF MAKING SAME

CROSS REFERENCE TO RELATED APPLICATIONS

This application is a continuation under 35 USC 120 of U.S. patent application Ser. No. 12/119,463 filed May 12, 2008 in the name of Tianniu Chen, et al. (issued May 4, 2010 as U.S. Pat. No. 7,709,384), which in turn is a continuation under 35 USC 120 of U.S. patent application Ser. No. 11/625,918 filed Jan. 23, 2007 in the name of Tianniu Chen, et al. (U.S. Pat. No. 7,371,878 issued May 13, 2008), which in turn is a continuation under 35 USC 120 of U.S. patent application Ser. No. 11/224,588 filed Sep. 12, 2005 in the name of Tianniu Chen, et al. (now U.S. Pat. No. 7,198,815 issued Apr. 3, 2007), which in turn is a continuation under 35 USC 120 of U.S. patent application Ser. No. 10/684,545 filed on Oct. 14, 2003 in the name of Tianniu Chen, et al. (now U.S. Pat. No. 6,960,675 issued Nov. 1, 2005). The disclosures of each of the aforementioned patent applications are hereby incorporated by reference, in their respective entireties, for all purposes.

BACKGROUND OF THE INVENTION

1. Field of the Invention

The present invention relates to tantalum-amido precursors useful in depositing Ta-containing material on a substrate, e.g., thin film layers of tantalum nitride or tantalum oxide, as well as to the synthesis of such precursors and to deposition methods employing same.

2. Description of the Related Art

Copper is of great interest for use in metallization of VLSI microelectronic devices because of its low resistivity and contact resistance, as well as its ability to enhance device performance (relative to aluminum metallization) by reducing RC time delays and thereby yielding faster microelectronic devices. Copper chemical vapor deposition (CVD) processes useful in large-scale manufacturing of microelectronic devices, e.g., in conformal filling of high aspect ratio inter-level vias in high density integrated circuits, are actively being developed and implemented by the electronics industry.

Although Cu CVD has enjoyed progressively wider usage in semiconductor manufacturing, various problems have resisted solution in the integration of copper in such microelectronic device applications. It is well established that copper diffuses relatively rapidly through many materials, including both metals and dielectrics, especially at temperatures above ~300° C., resulting in degradation of device performance and reliability, in some instances to the point of inoperability of the microelectronic device.

To inhibit diffusion of copper in microelectronic devices, barrier materials have been developed that separate copper metallization regions from vulnerable device regions, to ensure the long-term reliability of the copper-based metallurgy in integrated circuits (IC). Effective barrier materials generally must possess several characteristics, including a low diffusion coefficient for copper, low electrical resistivity, good thermal stability, effective adhesive interfaces, and the ability to form good nucleation surfaces to promote <111> texture in the deposited copper layer.

To achieve effective barrier performance, deposition of the barrier material desirably involves good step coverage in high-aspect-ratio device features, e.g., dual-damascene trench and via structures. With progressively increasing shrinkage of feature sizes in computer chips, CVD and atomic layer deposition (ALD) of the barrier material have proved advantageous over sputtering and physical vapor deposition (PVD) in achieving uniform-thickness conformal thin films with good step coverage in high-aspect ratio device features.

TaN and TaSiN have been demonstrated as suitable metal diffusion barrier materials. CVD of TaN is currently carried out using $Ta(NMe_2)_5$, penta(dimethylamino)tantalum (PDMAT). PDMAT is a solid source precursor that decomposes above 80° C. and has a limited volatility. As such, sublimation is necessary to deposit high purity tantalum-containing films, resulting in increased deposition system complexity and costs, relative to CVD utilizing liquid-phase source reagents.

$Ta(NEt_2)_5$, penta(diethylamino)tantalum (PDEAT) is a liquid, but it is unstable under elevated temperature conditions, readily decomposing to a tantalum imide species, $Ta(=NEt)(NEt_2)_3$, upon heating and therefore, unsatisfactory as a liquid source reagent for TaN barrier layer formation.

t-BuN=Ta$(NEt_2)_3$, tert-butylimino-tris-(diethylamino)tantalum (TBTDET) is a liquid at room temperature and has been proposed as a precursor for depositing TaN, but it has various unfavorable characteristics that limit its utility. Chief among these is the fact that deposition temperatures higher than 600° C. are needed to deposit suitably low resistivity films. Another problem with TBTDET is that too much carbon is incorporated in the deposited tantalum-containing film, and the resulting high carbon layers are highly resistive, and have low density and reduced effectiveness as diffusional barriers.

TaSiN has been proposed as a diffusion barrier material. CVD processes for the formation of this ternary barrier layer material have been the focus of associated development efforts. CVD of TaSiN has been carried out using PDMAT as the tantalum source and silane as the silicon source. $TaCl_5$ in combination with silane and ammonia also has been used for forming TaSiN films. Apart from hazards associated with handling pyrophoric gases such as silane, such approaches require dual source reactor configurations to accommodate the multiple precursor species ($TaCl_5$ or $Ta(NMe_2)_5$ as the tantalum reagent and silane as the silicon source). The use of dual source reactor configurations in turn significantly increases the cost and complexity of the semiconductor manufacturing operation, relative to the use of a single source reagent.

In all instances, the formation of a Ta-based diffusion barrier by chemical vapor deposition requires an effective CVD approach. The CVD process must achieve conformal coating of inter-level (<0.15 μm) vias and sidewall. Additionally, the CVD source reagent must be storage-stable, of appropriate volatility and vaporization characteristics, with good transport and deposition characteristics for production of high-purity, electronic quality thin films. CVD source reagents for such purpose are desirably liquid in character, to facilitate liquid delivery techniques that are consistent with effective volatilization and transport of the precursor vapor and the achievement of superior conformal films on the substrate.

Among various chemical vapor deposition techniques, atomic layer deposition (ALD) has emerged in recent years as a promising candidate for deposition of thin films in device structures with very small feature dimensions. ALD is carried out to achieve successive single-monolayer depositions, in which each separate deposition step theoretically goes to saturation at a single molecular or atomic monolayer thickness and self-terminates when the monolayer formation occurs on the surface of the substrate. Single-monolayer depositions are performed a number of times until a sufficiently thick film has been deposited on the substrate.

It would therefore be a significant advance in the art to provide tantalum precursors that are readily synthesized and suitable for use in vapor deposition processes such as ALD or other CVD techniques, that are robust, that possess good volatilization, transport and deposition characteristics, that are amenable to liquid delivery, e.g., by bubbling or direct liquid injection, and that produce tantalum-containing films such as TaN, $Ta_2O_5$, TaSiN and $BiTaO_4$, as well as other Ta-nitride and Ta-oxide films, of superior quality and performance characteristics.

SUMMARY OF THE INVENTION

The present invention relates generally to tantalum source reagents useful for forming Ta-containing material on a substrate, as well as to methods of making and using such tantalum source reagents.

In one aspect, the present invention relates to a precursor composition comprising at least one tantalum species selected from the group consisting of:

(i) tethered amine tantalum complexes of the formula $(\eta^2\text{-}R^3N(R^4)_nNR^5)Ta(NR^1R^2)_3$:

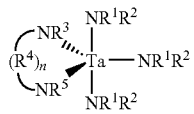

wherein:
each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

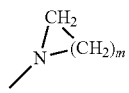

wherein m=1, 2, 3, 4, 5 or 6;
$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and
n is 1, 2, 3, or 4, but where $R^4$ is silylene, $C_1$-$C_4$ dialkylsilylene or $NR^8$, n must be 1; and (ii) tethered amine tantalum complexes of the formula $(\eta^2\text{-}R^3N(R^4)_nNR^5)_2Ta(NR^1R^2)$,

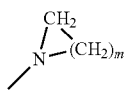

wherein:
each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

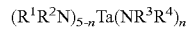

wherein m=1, 2, 3, 4, 5 or 6;
$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and
n is 1, 2, 3, or 4, but where $R^4$ is silylene, $C_1$-$C_4$ dialkylsilylene or $NR^8$, n must be 1; and (iii) tantalum amide compounds of the formula:

$$(R^1R^2N)_{5-n}Ta(NR^3R^4)_n$$

wherein:
each of $R^1$-$R^4$ is independently selected from the group consisting of $C_1$-$C_4$ alkyl, silyl, $C_3$-$C_8$ cycloalkyl, $C_1$-$C_4$ alkylsilyl, $C_6$-$C_{10}$ aryl, or alternatively $NR^1R^2$ or $NR^3R^4$ may be represented by the molecular moiety

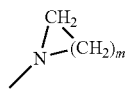

wherein m=1, 2, 3, 4, 5 or 6; and
n is 1, 2, 3, or 4.

In another aspect, the invention relates to specific compounds of the foregoing formulae, specifically, $\eta^2$-N,N'-dimethylethylenediamino-tris-dimethylaminotantalum, $\eta^2$-N,N'-diethylethylenediamino-tris-dimethylaminotantalum, $\eta^2$-N,N'-dimethylpropane-diamino-tris-dimethylaminotantalum and bis-diethylamino-tris-dimethylaminotantalum.

In a further aspect, the invention relates to a method of forming Ta material on a substrate from a precursor. The method includes vaporizing the precursor to form a precursor vapor, and contacting the precursor vapor with the substrate to form the Ta material thereon, wherein the precursor includes at least one tantalum species as described hereinabove.

Yet another aspect of the invention relates to a process for making tantalum complexes of formula (I):

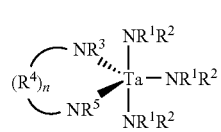

(I)

wherein:
each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

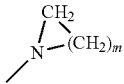

wherein m=1, 2, 3, 4, 5 or 6;
$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and
n is 1, 2, 3, or 4, but where $R^4$ is silylene, $C_1$-$C_4$ dialkylsilylene or $NR^8$, n must be 1;

such process including reacting a compound of formula (IV) with $LiNR^5(R^4)_nNR^3Li$:

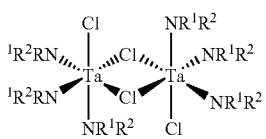

wherein $R^1$-$R^5$ and n are as defined above.

Still another aspect of the invention relates to a process for making a tantalum complex of formula II:

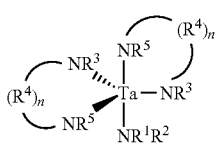

wherein:
each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

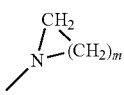

wherein m=1, 2, 3, 4, 5 or 6;
$R^4$ is selected from the group consisting of $C_1$-$C_4$ alkylene, silylene (—$SiH_2$—), $C_1$-$C_4$ dialkylsilylene and $NR^B$, wherein $R^8$ is selected from the group consisting of H, $C_3$-$C_8$ cycloalkyl and $C_1$-$C_4$ alkyl; and
n is 1, 2, 3, or 4, but where $R^4$ is silylene, $C_1$-$C_4$ dialkylsilylene or $NR^B$, n must be 1; and;

such process comprising:
reacting $TaX_5$ with $LiNR^5(R^4)_nNR^3Li$ to yield a compound of formula (V):

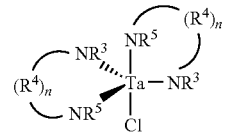

wherein $R^3$-$R^5$ and n are as defined above and X=Cl, Br or I; and
reacting the compound of formula (V) with $LiN(R^1R^2)$, wherein $R^1$ and $R^2$ are as defined above.

In a further aspect, the invention relates to a process for making a tantalum amide compound of the formula (III):

$$(R^1R^2N)_{5-n}Ta(NR^3R^4)_n \qquad (III)$$

wherein:
each of $R^1$-$R^4$ is independently selected from the group consisting of $C_1$-$C_4$ alkyl, silyl, $C_3$-$C_8$ cycloalkyl, $C_1$-$C_4$ alkylsilyl, $C_6$-$C_{10}$ aryl, or alternatively $NR^1R^2$ or $NR^3R^4$ may be represented by the molecular moiety

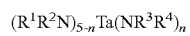

wherein m=1, 2, 3, 4, 5 or 6; and
n is 1, 2, 3, or 4.

such process comprising
reacting compound (IV) with $LiNR^3R^4$:

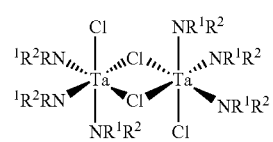

wherein $R^1$-$R^4$ are as defined above.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
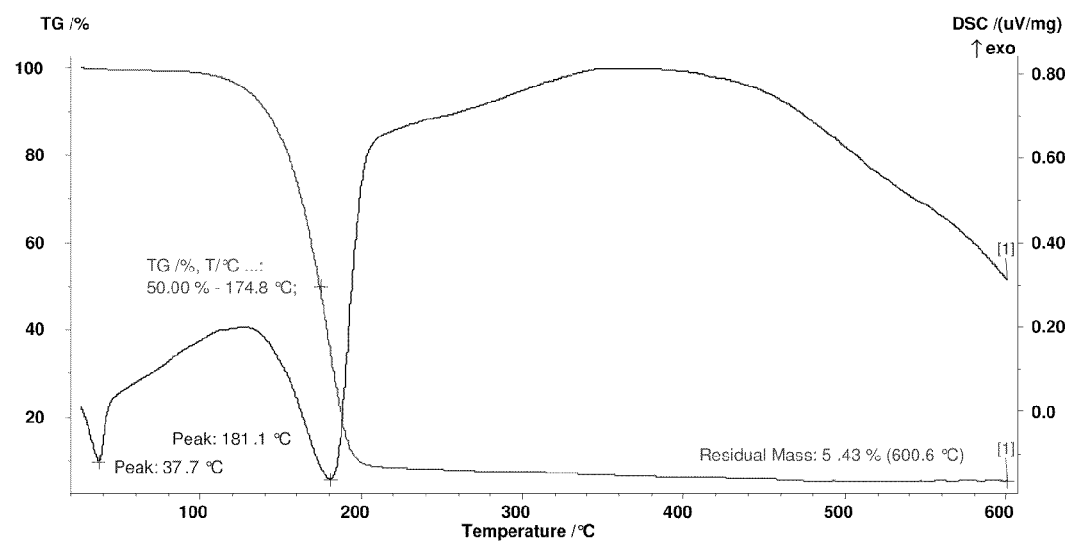
FIG. 1 is a Simultaneous Thermal Analysis (STA) plot of 5.15 mg ($\eta^2$-MeN($CH_2$)$_2$NMe)Ta(NMe$_2$)$_3$ (DEMAT) in Ar.

The present invention is based on the discovery of tantalum source reagents useful in forming Ta-based barrier layers on substrates, e.g., TaN, $Ta_2O_5$, TaSiN and $BiTaO_4$ barrier layers, for manufacture of microelectronic device structures such as integrated circuitry including copper metallization and/or ferroelectric layers.

The Ta precursors of the invention include tantalum species selected from the following group:

(i) tethered amine tantalum complexes of the formula ($\eta^2$-$R^3N(R^4)_nNR^5)Ta(NR^1R^2)_3$:

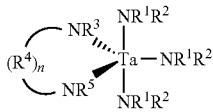

wherein:

each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

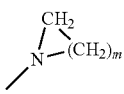

wherein m=1, 2, 3, 4, 5 or 6;

$R^4$ is selected from the group consisting of $C_1$-$C_4$ alkylene, silylene $C_1$-$C_4$ dialkylsilylene and $NR^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or $NR^8$, n must be 1;

(ii) tethered amine tantalum complexes of the formula ($\eta^2$-$R^3N(R^4)_nNR^5)_2Ta(NR^1R^2)$,

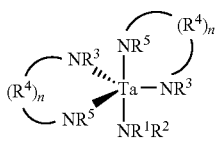

wherein:

each of $R^1$, $R^2$, $R^3$ and $R^5$ is independently selected from the group consisting of H, $C_1$-$C_4$ alkyl, silyl, $C_3$-$C_8$ cycloalkyl, $C_1$-$C_4$ alkylsilyl, $C_6$-$C_{10}$ aryl and nitrogen-containing groups such as $NR^6R^7$, wherein $R^6$ and $R^7$ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

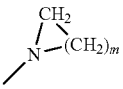

wherein m=1, 2, 3, 4, 5 or 6;

$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or $NR^8$, n must be 1; and (iii) tantalum amide compounds of the formula:

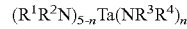

$(R^1R^2N)_{5-n}Ta(NR^3R^4)_n$ wherein:

each of $R^1$-$R^4$ is independently selected from the group consisting of $C_1$-$C_4$ alkyl, silyl, $C_3$-$C_8$ cycloalkyl, $C_1$-$C_4$ alkylsilyl, $C_6$-$C_{10}$ aryl, or alternatively $NR^1R^2$ or $NR^3R^4$ may be represented by the molecular moiety

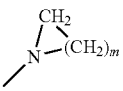

wherein m=1, 2, 3, 4, 5 or 6; and n is 1, 2, 3, or 4.

The tantalum precursors of the invention achieve a substantial advance in the art over the use of tantalum precursors previously employed for forming barrier layer films. Considering tantalum nitride as an example, the growth of tantalum nitride barrier layers desirably is carried out with precursors that are free of oxygen, so that the formation of tantalum oxide is avoided. Tantalum amides, which have preexisting Ta—N bonds, are therefore desirable in principle, but homoleptic tantalum amides such as $Ta(NMe_2)_5$ suffer from reduced volatility, as a result of the bridging of multiple metal centers through —$NMe_2$ groups (analogous to that observed for $Ta(OEt)_5$) and steric congestion around the Ta metal center.

By contrast, the tantalum precursors of the present invention have enhanced thermal stability and volatility as a result of their structures, which limit the degree of intermolecular interactions. For example, as compared to PDMAT with its two —$NMe_2$ groups, the use of tethered amine ligands ($\eta^2R^3N(R^4)_nNR^5$) in compounds of formula I below provides such monomeric tantalum amide compounds with a stable metallocyclic structure. Various tethered ligands can be employed. Ligand species of the formula $\eta^2$-$R^3N(R^4)_nNR^5$ wherein $R^3$ and $R^5$ are the same as or different from one another, and each is independently chosen from H, $C_1$-$C_4$ alkyl (e.g., Me, Et, t-Bu, i-Pr, etc.), aryl (e.g., phenyl, phenyl substituted with $C_1$-$C_4$ alkyl, halo, silyl or $C_1$-$C_4$ alkylsilyl, etc.), $C_3$-$C_8$ cycloalkyl, or a silicon-containing group such as silyl ($SiH_3$), $C_1$-$C_4$ alkylsilyl, (e.g., $SiMe_3$, $Si(Et)_3$, $Si(i-Pr)_3$, $Si(t-Bu)_3$) and alkyl(alkylsilyl)silyl (e.g., $Si(SiMe_3)_x$ $(Me)_{3-x}$), $R_4$ can be $C_1$-$C_4$ alkylene (e.g. methylene, ethylene, etc.), silylene (e.g. —$SiH_2$—), $C_1$-$C_4$ dialkylsilyl (e.g. $Si(CH_3)_2$, etc.) or alkylamine (e.g. $NCH_3$, etc.), appropriately selected to confer a specific volatility, are preferred, wherein n is 1, 2, 3, or 4 to provide stable chelating ring structures.

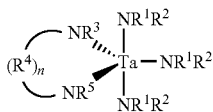
(I)

The tantalum amide compounds of formula II below feature two of the chelating ($\eta^2$-$R^3N(R^4)_nNR^5$) ligands, wherein n and the various R groups are as defined in connection with formula I hereinabove.

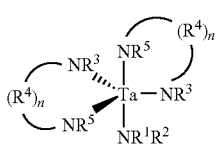
(II)

Another class of tantalum compounds of the invention include tantalum amides that are unsymmetrical in character, and utilize $(R^1R^2N)_{5-n}$ and $(NR^3R^4)_n$ as ligands of mixed ligand complexes of formula III:

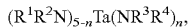

$(R^1R^2N)_{5-n}Ta(NR^3R^4)_n$, in which each of $R^1$-$R^4$ is independently chosen from $C_1$-$C_4$ alkyl (e.g., Me, Et, t-Bu, i-Pr, etc.), $C_6$-$C_{10}$ aryl (e.g., phenyl, phenyl substituted with $C_1$-$C_4$ alkyl, halo, silyl or $C_1$-$C_4$ alkylsilyl, etc.), $C_3$-$C_8$ cycloalkyl or a silicon-containing group such as silyl ($SiH_3$), $C_1$-$C_4$ alkylsilyl, (for example, $SiMe_3$, $Si(Et)_3$, $Si(i-Pr)_3$, $Si(t-Bu)_3$) and alkyl(alkylsilyl)silyl (e.g., $Si(SiMe_3)_x(Me)_{3-x}$), and n is 1, 2, 3, or 4. Alternatively, $NR^1R^2$ or $NR^3R^4$ may be represented by the molecular moiety

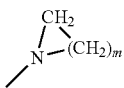

wherein m=1, 2, 3, 4, 5 or 6.

The Ta source reagents of the invention have suitable volatility characteristics for applications such as CVD.

In application to vapor deposition processes such as liquid delivery, atomic layer deposition or other chemical vapor deposition techniques, the precursors of the invention may be employed in neat liquid form, or alternatively such precursors may be utilized in formulations, e.g., in a solution or suspension of the precursor in a compatible liquid solvent or suspending medium, such as the solvent compositions disclosed in U.S. Pat. No. 5,820,664, issued Oct. 13, 1998, in the names of Robin A. Gardiner et al.

The term "liquid delivery" refers to the liquid form of the precursor composition being employed for delivery of the material to be deposited on the substrate in the vapor deposition process. When the precursor compound is a liquid phase neat material, it is vaporized to produce a corresponding precursor vapor that is then is transported to the deposition chamber, to form a film or coating of the deposition species on the substrate. Alternatively, the source reagent may be dissolved or suspended in a liquid that is vaporized to place the source reagent in the vapor phase for the deposition operation.

The solvent for such purpose can be any suitable solvent medium, e.g., a single-component solvent, or a solvent mixture of multiple solvent species. The solvent in one embodiment of the invention is selected from among $C_6$-$C_{10}$ alkanes, $C_6$-$C_{10}$ aromatics, and compatible mixtures thereof. Illustrative alkane species include hexane, heptane, octane, nonane and decane. Preferred alkane solvent species include $C_8$ and $C_{10}$ alkanes. Preferred aromatic solvent species include toluene and xylene.

It will be appreciated that various syntheses are useful for preparation of tantalum source compounds of the present invention, as will be readily apparent to those of ordinary skill in the art. Illustrative synthetic methods for production of compounds within the broad scope of the present invention are set out below by way of example, it being understood that compounds of the invention are amenable to manufacture by various other synthesis routes and methods within the skill in the art, and that the illustrative synthesis methods set out below are therefore not to be limitingly construed as regards the scope of the invention.

Synthesis Reaction Schemes for Compounds of Formula I

One illustrative synthesis scheme for compounds of formula I hereof is set out below:

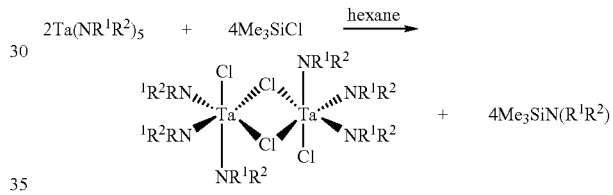

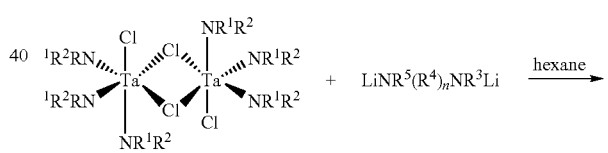

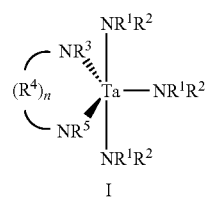

Alternatively, compounds of formula I may be synthesized as follows:

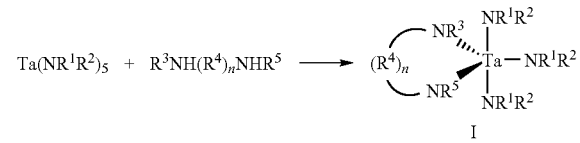

Synthesis Reaction Schemes for Compounds of Formula II

One illustrative synthesis scheme for compounds of formula II hereof is set out below:

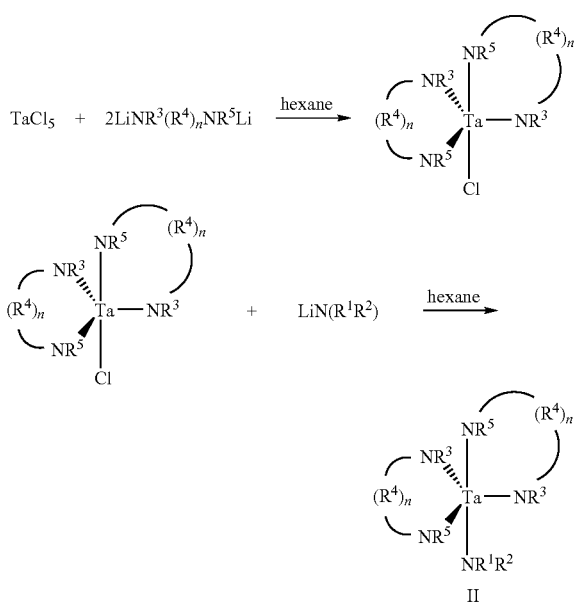

Alternatively, compounds of formula II may be synthesized as follows:

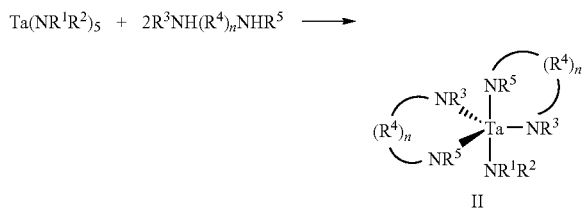

Synthesis Reaction Schemes for Compounds of Formula III

An illustrative synthesis scheme for compounds of formula III hereof is set out below:

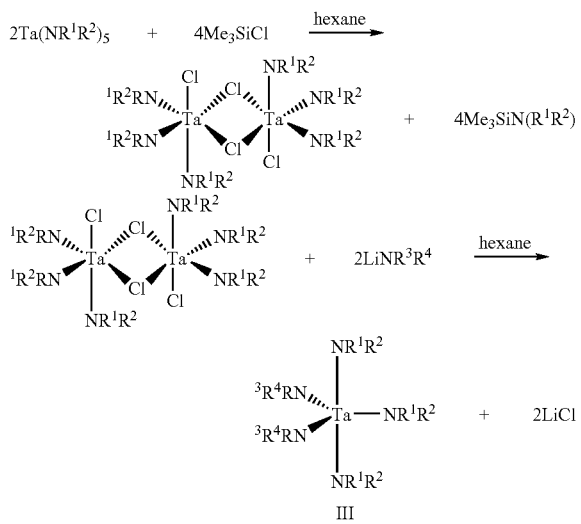

The present invention also contemplates the use of silyl amides with as single source precursors useful in forming TaSiN layers on substrates in a direct and cost-effective manner. Examples include precursors of the general formula III:

$$(R^1R^2N)_{5-n}Ta(NR^3R^4)_n,$$

in which each of $R^1$-$R^4$ is independently chosen from $C_1$-$C_4$ alkyl (e.g., Me, Et, t-Bu, i-Pr, etc.), $C_6$-$C_{10}$ aryl (e.g., phenyl, phenyl substituted with $C_1$-$C_4$ alkyl, halo, silyl or $C_1$-$C_4$ alkylsilyl, etc.), or a silicon-containing group such as silyl ($SiH_3$), $C_1$-$C_4$ alkylsilyl, (for example, $SiMe_3$, $Si(Et)_3$, $Si(i-Pr)_3$, $Si(t-Bu)_3$) and alkyl(alkylsilyl)silyl (e.g., $Si(SiMe_3)_x(Me)_{3-x}$), and n is 1, 2, 3, or 4, with the proviso that at least one of $R^1$, $R^2$, $R^3$ and $R^4$ is a silicon-containing group. The number of silicon-containing R groups can be varied as necessary or desirable to control the amount of silicon in the film.

For liquid delivery deposition of Ta-based films or coatings on a substrate, the source reagent material is provided as a liquid starting material, e.g., as a neat liquid-phase compound, or in a suitable formulation including a solvent medium suitable for dissolving or suspending the precursor compound, and the liquid starting material then is vaporized to form the precursor vapor for the vapor deposition process.

The vaporization may be carried out by injection of the liquid, e.g., in fine jet, mist or droplet form, into a hot zone at an appropriate temperature for vaporization of the source reagent liquid. Such injection may be carried out with a nebulization or atomization apparatus of conventional character, producing a dispersion of finely-divided liquid particles, e.g., of sub-micron to millimeter diameter. The dispersed liquid particles may be directed at a substrate at a sufficiently high temperature to decompose the source reagent and produce a coating of the desired Ta-based material on the substrate.

Alternatively, the liquid may be dispensed from a suitable supply vessel containing same, so that it issues onto a volatilization element, such as a screen, grid or other porous or foraminous structure, which is heated to a sufficiently high temperature to cause the liquid to flash volatilize into the vapor phase, as described in U.S. Pat. No. 5,204,314 to Peter S. Kirlin, et al. and U.S. Pat. No. 5,711,816 to Peter S. Kirlin, et al.

Regardless of the manner of volatilization of the source reagent, the vapor thereof is flowed to contact the substrate on which the Ta-based material is to be deposited, at appropriate deposition conditions therefor, as are readily determinable within the skill of the art without undue experimentation, by the expedient of varying the process conditions (temperature, pressure, flow rate, etc.) and assessing the character and suitability of the resulting deposited material.

The deposition of the Ta material on the substrate may be carried out in the broad practice of the invention in any suitable manner, as regards the precursor compound of the invention, and the substrate and process conditions employed. For example, carrier gases may be employed for transport of the precursor vapor, such as inert gases (e.g., helium, argon, etc.) or a carrier gas appropriate to provide a desired ambient in the deposition chamber (e.g., an oxygen-containing gas, nitrogen, or other suitable carrier gas species).

In one embodiment of the invention, atomic layer deposition (ALD) is employed for depositing the Ta-based material on the substrate. For example, the ALD process may be carried out in which the substrate is exposed sequentially and alternately to at least two mutually reactive reactants. In such approach, the substrate is exposed to the first species and the first species is deposited onto the surface of the substrate until the surface is occupied with a monolayer of the first species (saturation). Following surface saturation, the supply of the first deposited species is cut-off and the reaction chamber is evacuated and/or purged to remove the traces of the first species from the gas phase. Next, the substrate is exposed to the second species which interacts with the deposited first species until the monolayer of the first species has fully interacted with the second species and the surface of the substrate is covered with a monolayer of the product of the first and second species (saturation). Following saturation by the second species, the supply of the second species is cut-off and the reaction chamber is evacuated and/or purged to remove the traces of non-reacted second species from the gas phase. This cycle can be repeated a number of times until a sufficiently thick film has been deposited onto the substrate. Notably, more than two species may be used, e.g., for the deposition of ternary or more complicated compounds or multilayers.

The features and advantages of the invention are more fully shown by the following non-limiting examples.

Example 1

In this example, $\eta^2$-N,N'-dimethylethylenediamino-tris-dimethylaminotantalum, $(\eta^2$-MeN$(CH_2)_2$NMe)Ta$(NMe_2)_3$ (DEMAT), was synthesized at high purity and in good yield.

The synthesis of DEMAT was carried out using standard Schlenk techniques. 15.8 mL n-butyl lithium (1.6 M in hexanes, 0.025 mol) was added to a 100 mL Schlenk flask immersed in an ice bath and charged with 1.11 g N,N'-dimethylethylenediamine (0.013 mol) in 50 mL hexanes. White precipitation appeared after the addition started and the reaction was exothermic. The reaction mixture comprising MeNLi$(CH_2)_2$LiNMe was allowed to warm to room temperature. Next the MeNLi$(CH_2)_2$LiNMe mixture was added dropwise to 4.39 g $[(MeN)_3TaCl_2]_2$ (5.71 mmol) in 100 mL hexanes at room temperature and stirred overnight. Following filtration, the dark brown filtrate was recovered. The volatiles from the filtrate were removed in vacuo at room temperature followed by vacuum distillation at 79° C. and 50 mTorr to yield 3.06 g of red orange $(\eta^2$-MeN$(CH_2)_2$NMe)Ta$(NMe_2)_3$ (DEMAT) (59% yield). Atomic percentage calculated for TaC$_{10}$H$_{28}$N$_5$: C, 30.08%; H, 7.07%; N, 17.54%. Found: C, 29.89%; H, 6.94%; N, 17.52%.

FIG. 1 shows that DEMAT is thermally-stable up to its boiling temperature and undergoes complete material transport below 200° C. Further, DEMAT is volatile enough and thermally stable enough to be purified by vacuum distillation. In contrast, PDEAT and pentaethylmethylaminotantalum (PEMAT) are unstable and cannot be purified by vacuum distillation. As such, DEMAT exhibits advantages over PDMAT, PEMAT, and PDEAT in terms of thermal stability and volatility.

Figure 2:
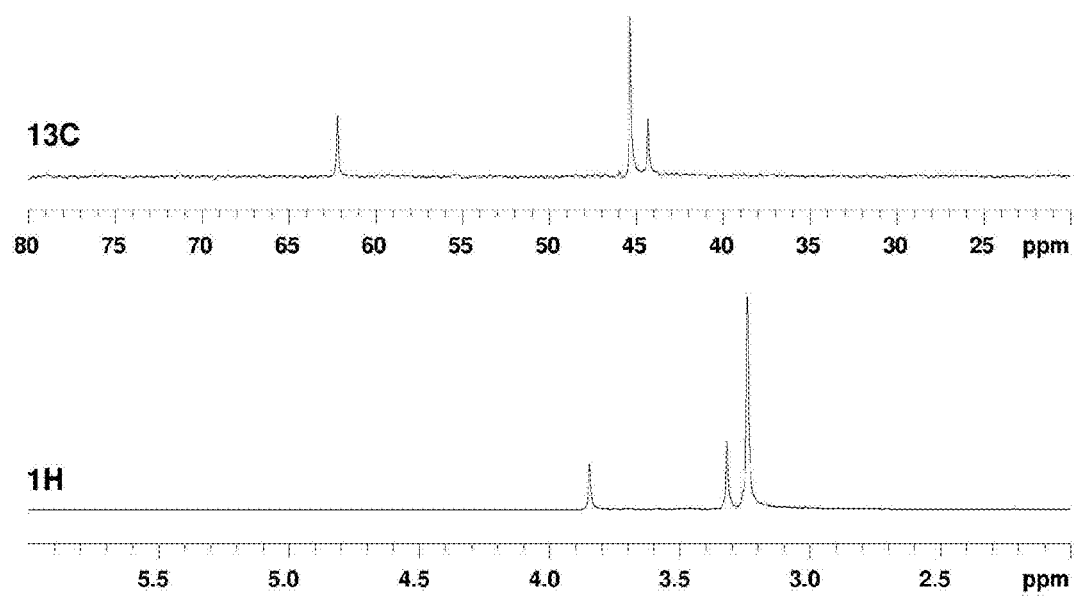
FIG. 2 is a $^1$H and $^{13}$C NMR plot for ($\eta^2$-MeN($CH_2$)$_2$NMe)Ta(NMe$_2$)$_3$ (DEMAT) in benzene-$d_6$.

FIG. 2 shows the $^1$H and $^{13}$C NMR plot of DEMAT in benzene-d$_6$ at 21° C. $^1$H NMR: δ 3.85 (s, 4H, CH$_3$N(CH$_2$)$_2$—); 3.33 (s, 6H, CH$_3$N—); 3.24 (s, 18H, (CH$_3$)$_2$N—). $^{13}$C NMR plot: δ 62.20 (CH$_3$N(CH$_2$)$_2$—); 45.36 ((CH$_3$)$_2$N—); 44.33 (CH$_3$N(CH$_2$)$_2$—).

Example 2

In this example, $\eta^2$-N,N'-diethylethylenediamino-tris-dimethylaminotantalum, $(\eta^2$-EtN$(CH_2)_2$NEt)Ta$(NMe_2)_3$ (DEMAT), was synthesized at high purity and in good yield.

The synthesis of $(\eta^2$-EtN$(CH_2)_2$NEt)Ta$(NMe_2)_3$ was carried out using standard Schlenk techniques. 13.4 mL n-butyl lithium (1.6 M in hexanes, 0.021 mol) was added to a 250 mL Schlenk flask immersed in an ice bath and charged with 1.11 g N,N'-diethylethylenediamine (0.011 mol) in 100 mL hexanes. White precipitation appeared after the addition started and the reaction was exothermic. The reaction mixture comprising EtNLi$(CH_2)_2$LiNEt was allowed to warm to room temperature. Next the EtNLi$(CH_2)_2$LiNEt mixture was added dropwise to 4.14 g $[(MeN)_3TaCl_2]_2$ (5.39 mmol) in 100 mL hexanes at room temperature and stirred overnight. Following filtration, the dark brown filtrate was recovered. The volatiles from the filtrate were removed in vacuo at room temperature followed by vacuum distillation at 77° C. and 65 mTorr to yield 2.01 g of golden yellow liquid $(\eta^2$-EtN$(CH_2)_2$NEt)Ta$(NMe_2)_3$ (44% yield). Atomic percentage calculated for TaC$_{12}$H$_{32}$N$_5$: C, 33.72%; H, 7.55%; N, 16.39%. Found: C, 33.42%; H, 7.46%; N, 16.22%.

Figure 3:
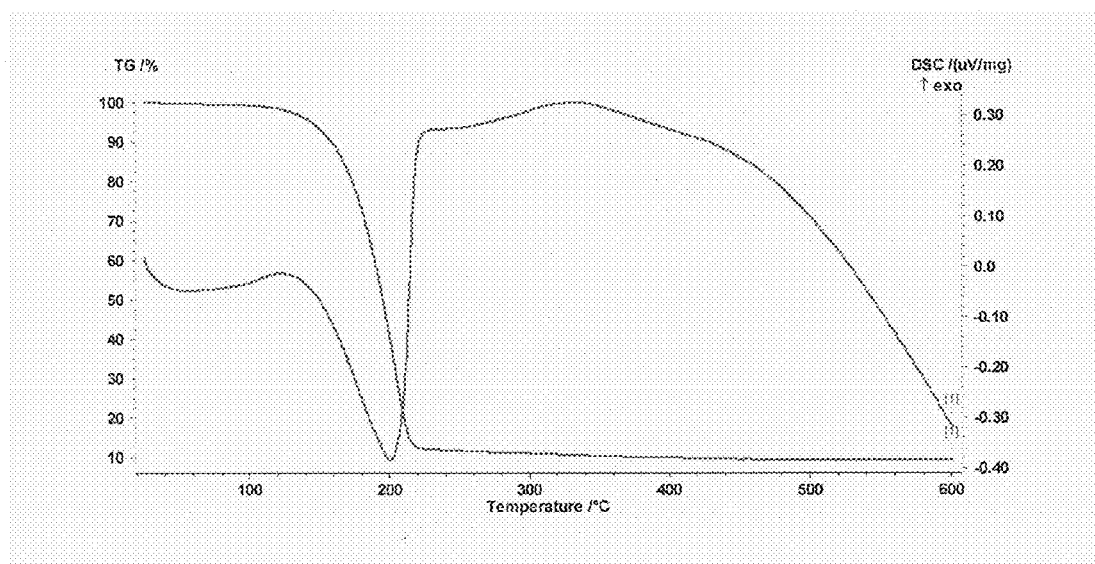
FIG. 3 is an STA plot of 9.530 mg ($\eta^2$-EtN($CH_2$)$_2$NEt)Ta(NMe$_2$)$_3$.

FIG. 3 shows that $(\eta^2$-EtN$(CH_2)_2$NEt)Ta$(NMe_2)_3$ is thermally-stable up to its boiling temperature and undergoes complete material transport below 200° C. Further, $(\eta^2$-EtN$(CH_2)_2$NEt)Ta$(NMe_2)_3$ is a liquid and thus is volatile enough and thermally stable enough to be purified by vacuum distillation. As such, $(\eta^2$-EtN$(CH_2)_2$NEt)Ta$(NMe_2)_3$ exhibits advantages over PDMAT, PEMAT, and PDEAT in terms of thermal stability and volatility.

Figure 4:
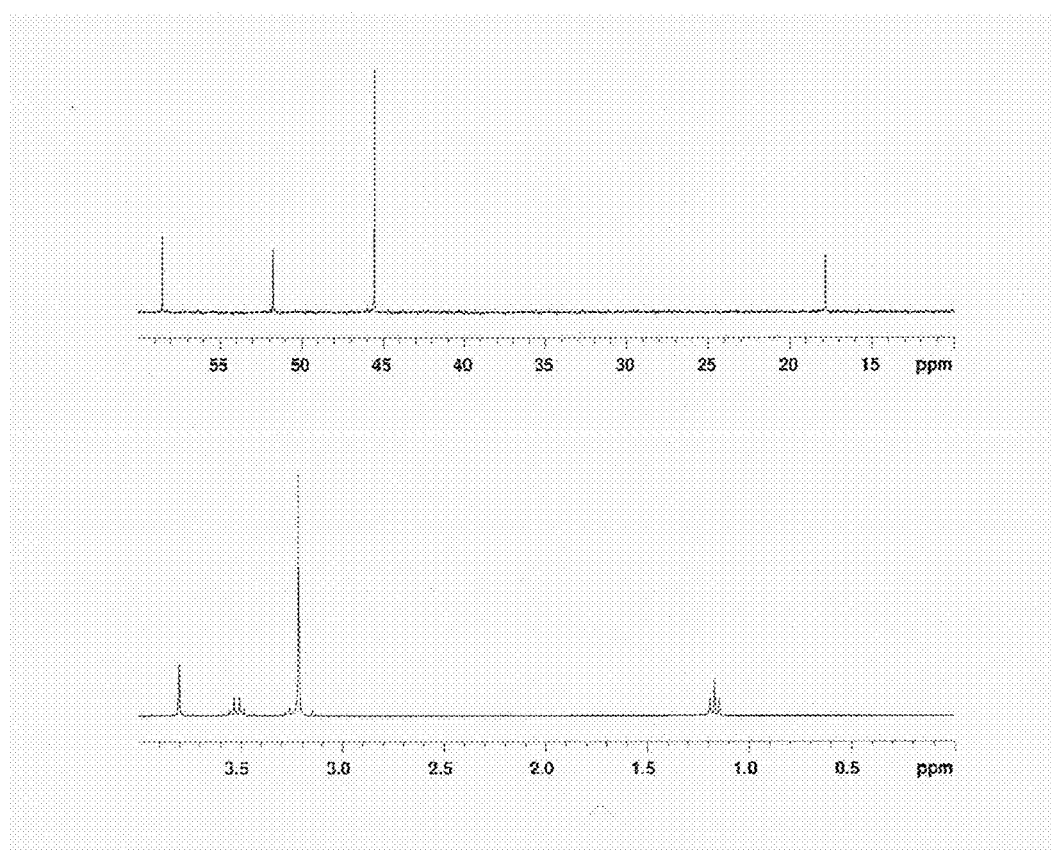
FIG. 4 is a $^1$H NMR plot for ($\eta^2$-EtN($CH_2$)$_2$NEt)Ta(NMe$_2$)$_3$ in benzene-$d_6$.

FIG. 4 shows the $^1$H and $^{13}$C NMR plot of $(\eta^2$-EtN$(CH_2)_2$NEt)Ta$(NMe_2)_3$ in benzene-d$_6$ at 21° C. $^1$H NMR: δ 3.80 (s, 4H, CH$_3$CH$_2$N(CH$_2$)$_2$—); 3.52 (q, 4H, CH$_3$CH$_2$N—); 3.22 (s, 18H, (CH$_3$)$_2$N—); 1.17 (t, 6H, CH$_3$CH$_2$N—). $^{13}$C NMR plot: δ 58.54 (CH$_3$CH$_2$N(CH$_2$)$_2$—); 51.76 ((CH$_3$CH$_2$N(CH$_2$)$_2$—); 45.41 ((CH$_3$)$_2$N—); 17.80 (CH$_3$CH$_2$N(CH$_2$)$_2$—).

Example 3

In this example, $\eta^2$-N,N'-dimethylpropanediamino-tris-dimethylaminotantalum, $(\eta^2$-MeN$(CH_2)_3$NMe)Ta$(NMe_2)_3$, was synthesized at high purity and in good yield.

The synthesis of $(\eta^2$-MeN$(CH_2)_3$NMe)Ta$(NMe_2)_3$ was carried out using standard Schlenk techniques. 16.4 mL n-butyl lithium (1.6 M in hexanes, 0.026 mol) was added to a 100 mL Schlenk flask immersed in an ice bath and charged with 1.34 g N,N'-dimethylpropanediamine (0.013 mol) in 50 mL hexanes. White precipitation appeared after the addition started and the reaction was exothermic. The reaction mixture comprising MeNLi$(CH_2)_3$LiNMe was allowed to warm to room temperature. Next the MeNLi$(CH_2)_3$LiNMe mixture was added dropwise to 5.02 g $[(MeN)_3TaCl_2]_2$ (6.54 mmol) in 30 mL hexanes at room temperature and stirred and refluxed at 80° C. overnight. Following filtration, the dark brown filtrate was recovered. The volatiles from the filtrate were removed in vacuo at room temperature followed by vacuum distillation at 85° C. and 50 mTorr to yield 2.05 g of yellow orange liquid $(\eta^2$-MeN$(CH_2)_3$NMe)Ta$(NMe_2)_3$ (38% yield). Atomic percentage calculated for TaC$_{11}$H$_{30}$N$_5$: C, 31.96%; H, 7.32%; N, 16.94%. Found: C, 31.74%; H, 7.46%; N, 16.82%.

Figure 5:
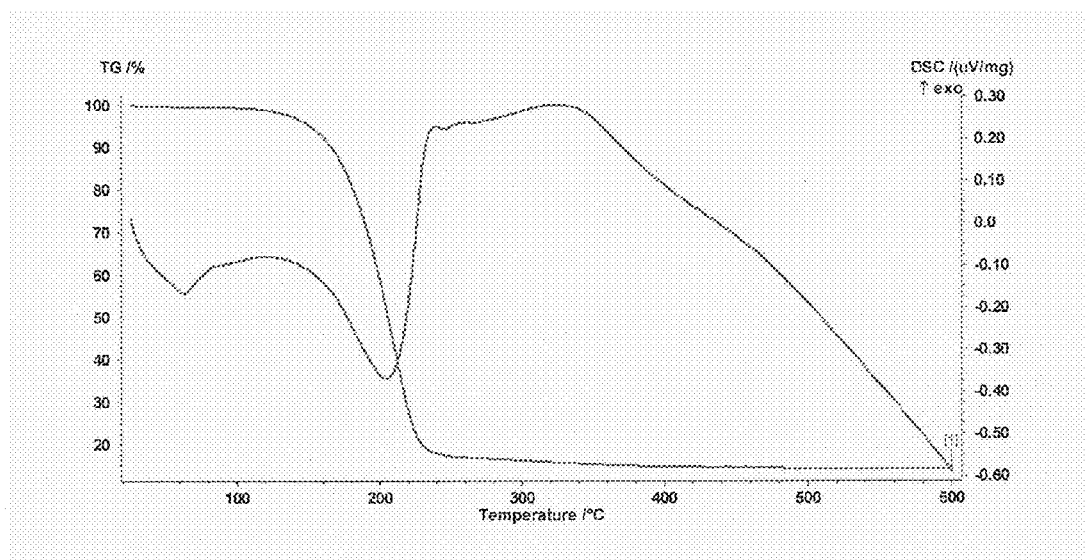
FIG. 5 is an STA plot of 12.141 mg ($\eta^2$-MeN($CH_2$)$_3$NMe)Ta(NMe$_2$)$_3$.

FIG. 5 shows that $(\eta^2$-MeN$(CH_2)_3$NMe)Ta$(NMe_2)_3$ is thermally-stable up to its boiling temperature and undergoes complete material transport below 210° C. Further, $(\eta^2$-MeN$(CH_2)_3$NMe)Ta$(NMe_2)_3$ is volatile enough and thermally stable enough to be purified by vacuum distillation. As such, $(\eta^2$-MeN$(CH_2)_3$NMe)Ta$(NMe_2)_3$ exhibits advantages over PDMAT, PEMAT, and PDEAT in terms of thermal stability and volatility.

Figure 6:
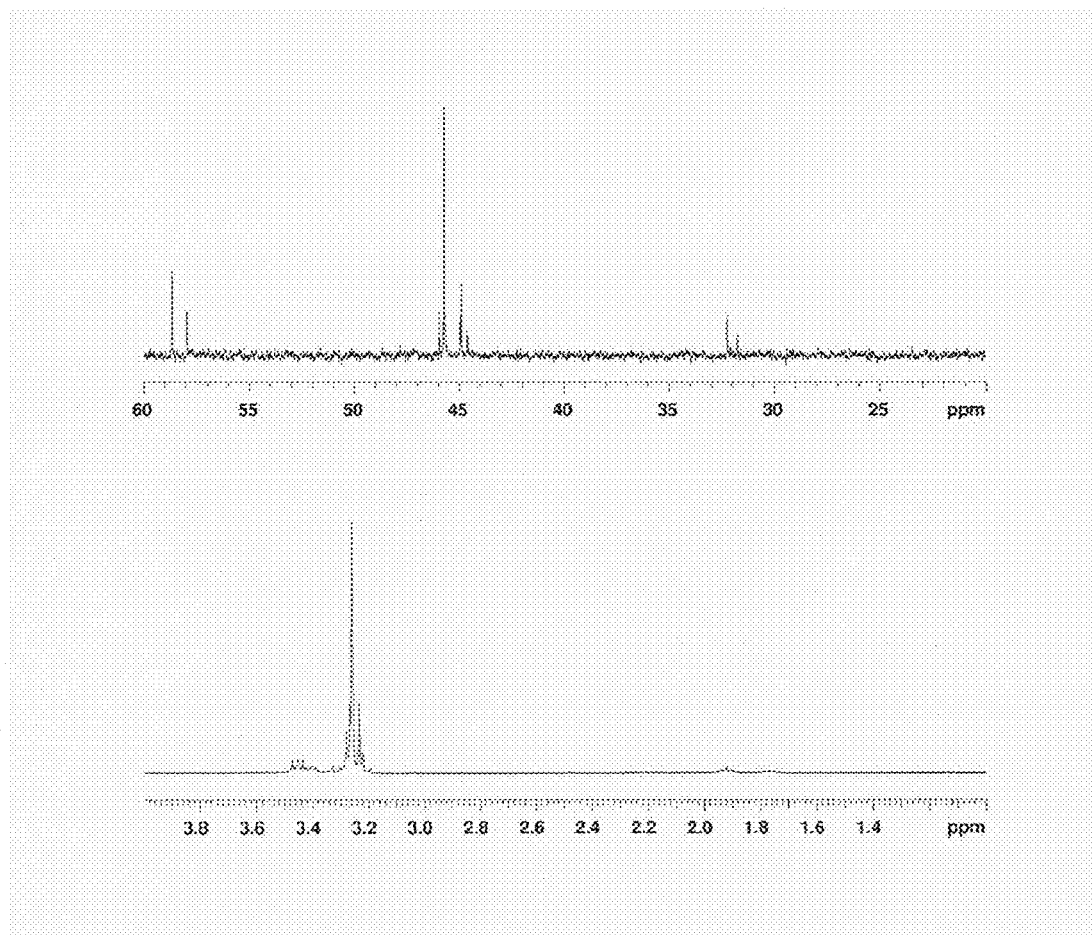
FIG. 6 is a $^1$H NMR plot for ($\eta^2$-MeN($CH_2$)$_3$NMe)Ta(NMe$_2$)$_3$ in benzene-$d_6$.

FIG. 6 shows the $^1$H and $^{13}$C NMR plot of $(\eta^2$-MeN$(CH_2)_3$NMe)Ta$(NMe_2)_3$ in benzene-d$_6$ at 21° C. $^1$H NMR: δ 3.44 (m, br, 4H, CH$_3$NCH$_2$—); 3.26 (s, 18H, (CH$_3$)$_2$N—); 3.22 (s, 6H, CH$_3$NCH$_2$—); 1.85 (m, 2H, CH$_3$NCH$_2$CH$_2$—). $^{13}$C NMR plot: δ 58.60, 57.88 (CH$_3$NCH$_2$—); 45.88, 45.66

((CH₃)₂N—); 44.90, 44.61 (CH₃NCH₂—); 32.23, 31.74 (CH₃NCH₂CH₂—). The NMR spectra are consistent with the assigned structure. The complicated patterns in the ¹H spectra are attributable to cis- (when the —NMe(CH₂)₃MeN— ligand occupies the equatorial positions in the trigonal bipyramidal geometry) and trans-isomers (when the —NMe(CH₂)₃MeN— ligand occupies the axial positions in the trigonal bipyramidal geometry) in the solution:

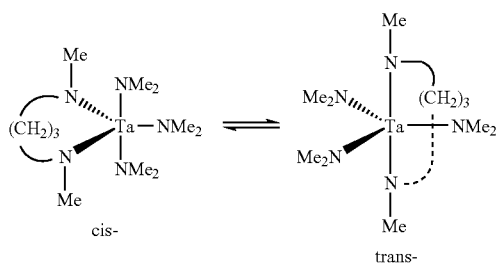

Example 4

In this example, bis-diethylamino-tris-dimethylaminotantalum, (NEt₂)₂Ta(NMe₂)₃ was synthesized in high purity and in good yield. The synthesis of (NEt₂)₂Ta(NMe₂)₃ was carried out using standard Schlenk techniques. 32.2 mL n-butyl lithium (1.6 M in hexanes, 0.052 mol) was added to a 250 mL Schlenk flask immersed in an ice water bath and charged with 5.34 mL diethylamine (3.78 g, 0.052 mol) in 50 mL hexanes. White precipitation appeared after the addition started and the reaction was exothermic. The reaction mixture comprising LiNEt₂ was allowed to warm to room temperature. Next, the LiNEt₂ mixture was added dropwise to 4.51 g [(MeN)₃TaCl₂]₂ (5.87 mmol) in 100 mL hexanes at room temperature and stirred overnight. Following filtration, the dark brown filtrate was recovered. The volatiles from the filtrate were removed in vacuo at room temperature to yield 4.10 g of dark yellow (NEt₂)₂Ta(NMe₂)₃ (76% yield). Atomic percentage calculated for TaC₁₄H₃₈N₅: C, 36.76%; H, 8.37%; N, 15.31%. Found: C, 36.56%; H, 8.30%; N, 14.97%.

Figure 7:
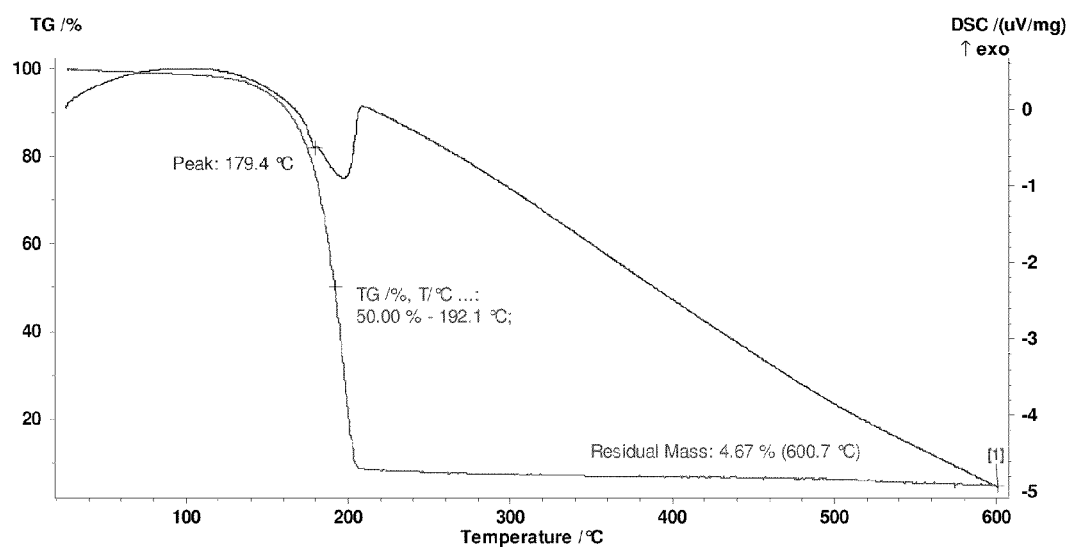
FIG. 7 is an STA plot of 6.28 mg (NEt$_2$)$_2$Ta(NMe$_2$)$_3$ in Ar.

FIG. 7 shows that (NEt₂)₂Ta(NMe₂)₃ is stable to heat up to its boiling temperature and undergoes complete material transport below 200° C.

Figure 8:
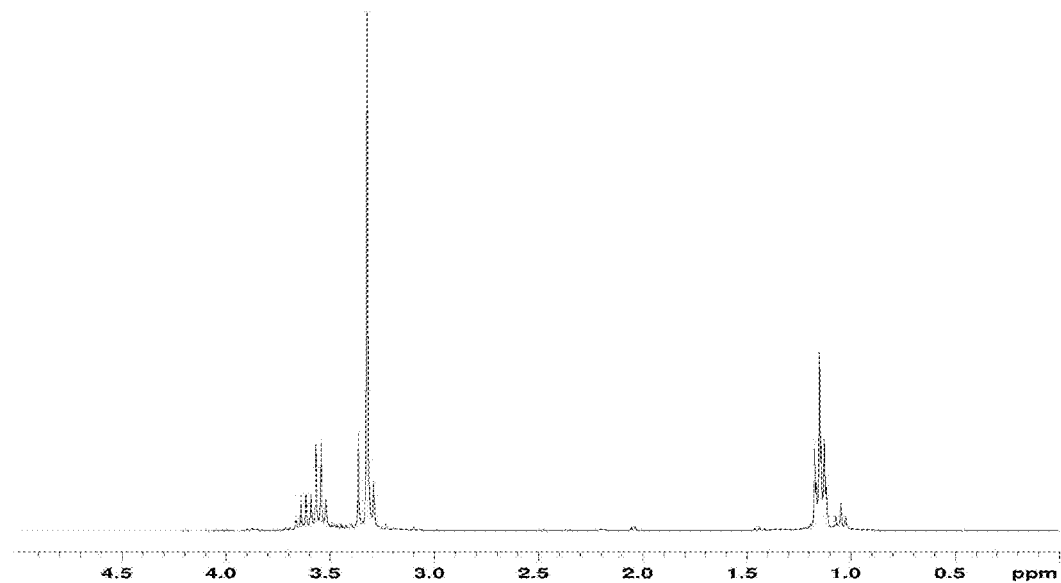
FIG. 8 is a $^1$H NMR plot for (NEt$_2$)$_2$Ta(NMe$_2$)$_3$ in toluene-$d_8$.

FIG. 8 shows the ¹H NMR plot of (NEt₂)₂Ta(NMe₂)₃ in toluene-d₈ at 21° C. ¹H NMR: δ 3.56 (m, 8H, CH₃CH₂N—); 3.29 (m, 18H, (CH₃)₂N—); 1.14 (m, 12H, CH₃CH₂N—). ¹³C NMR: δ 47.64, 46.69 (CH₃CH₂N—); 47.31, 47.09 ((CH₃)₂N—); 16.7, 16.0 (CH₃CH₂N—). The NMR spectra are consistent with the assigned structure; the complicated patterns in the ¹H spectra were attributable to cis- and trans-isomers in the solution:

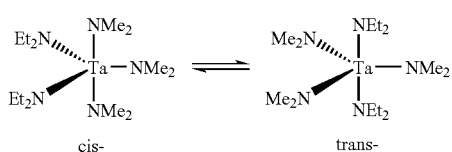

While the invention has been described illustratively herein with respect to specific aspects, features and embodiments thereof, it is to be appreciated that the utility of the invention is not thus limited, but rather extends to and encompasses other aspects, features and embodiments, such as will readily suggest themselves to those of ordinary skill in the art, based on the disclosure herein. The invention therefore is intended to be broadly construed and interpreted, as including all such aspects, features and alternative embodiments within the spirit and scope of the claims set forth hereafter.

What is claimed is:

1. A method of depositing a TaSiN film on a substrate, comprising volatilizing precursor material to form precursor vapor, and contacting the substrate with said precursor vapor to deposit said TaSiN film thereon, wherein said precursor material includes a tantalum- and nitrogen-containing precursor, and a silicon source comprising a silicon precursor selected from among (a) said tantalum- and nitrogen-containing precursor, wherein said tantalum- and nitrogen-containing precursor contains at least one silicon-containing group, and (b) a silicon precursor that is different from said tantalum- and nitrogen-containing precursor, and wherein said tantalum- and nitrogen-containing precursor is selected from the group consisting of:

(i) tethered amine tantalum complexes of the formula (I):

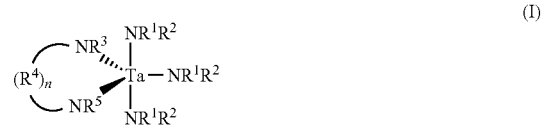

wherein:

each of R¹, R², R³ and R⁵ is independently selected from the group consisting of H, C₁-C₄ alkyl, silyl, C₃-C₈ cycloalkyl, C₁-C₄ alkylsilyl, C₆-C₁₀ aryl and nitrogen-containing groups such as NR⁶R⁷, wherein R⁶ and R⁷ are the same as or different from one another and each is independently selected from the group consisting of H, C₁-C₄ alkyl, and C₃-C₈ cycloalkyl, or alternatively NR¹R² may be represented by the molecular moiety

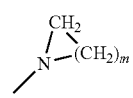

wherein m=1, 2, 3, 4, 5 or 6;

R⁴ is selected from the group consisting of C₁-C₄ alkylene, silylene (—SiH₂—), C₁-C₄ dialkylsilylene and NR⁸, wherein R⁸ is selected from the group consisting of H, C₃-C₈ cycloalkyl and C₁-C₄ alkyl; and n is 1, 2, 3, or 4, but where R⁴ is silylene, C₁-C₄ dialkylsilylene or NR⁸, n must be 1;

(ii) tethered amine tantalum complexes of the formula (II):

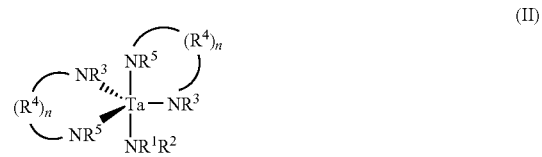

wherein:

each of R¹, R², R³ and R⁵ is independently selected from the group consisting of H, C₁-C₄ alkyl, silyl, C₃-C₈ cycloalkyl, C₁-C₄ alkylsilyl, C₆-C₁₀ aryl and nitrogen-containing groups such as NR⁶R⁷, wherein R⁶ and R⁷ are the same as or different from one another and each is independently selected from the group consisting of H, $C_1$-$C_4$ alkyl, and $C_3$-$C_8$ cycloalkyl, or alternatively $NR^1R^2$ may be represented by the molecular moiety

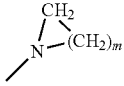

wherein m=1, 2, 3, 4, 5 or 6;

$R^4$ is selected from the group consisting of $C_1$-$C_4$ alkylene, silylene (—$SiH_2$—), $C_1$-$C_4$ dialkylsilylene and $NR^8$, wherein $R^8$ is selected from the group consisting of H, $C_3$-$C_8$ cycloalkyl and $C_1$-$C_4$ alkyl; and n is 1, 2, 3, or 4, but where $R^4$ is silylene, $C_1$-$C_4$ dialkylsilylene or $NR^8$, n must be 1; and (iii) tantalum amide compounds of the formula (III):

$$(R^1R^2N)_{5-n}Ta(NR^3R^4)_n \qquad (III)$$

wherein:

at least one of $NR^1R^2$ and $NR^3R^4$ may be represented by the molecular moiety

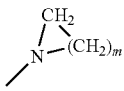

wherein m=1, 2, 3, 4, 5 or 6, and wherein when only one of $NR^1R^2$ and $NR^3R^4$ is said molecular moiety

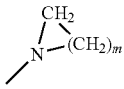

the other of $NR^1R^2$ and $NR^3R^4$ has substituents $R^1$ and $R^2$ in the case of $NR^1R^2$ and $R^3$ and $R^4$ in the case of $NR^3R^4$ which are the same as or different from one another and each is independently selected from the group consisting of $C_1$-$C_4$ alkyl, silyl, $C_3$-$C_8$ cycloalkyl, $C_1$-$C_4$ alkylsilyl, and $C_6$-$C_{10}$ aryl, and n is 1, 2, 3, or 4.

2. The method of claim 1, wherein the precursor material comprises a solvent for said tantalum- and nitrogen-containing precursor.

3. The method of claim 2, wherein said solvent comprises a solvent species selected from the group consisting of $C_6$-$C_{10}$ alkanes, $C_6$-$C_{10}$ aromatics, and compatible mixtures thereof.

4. The method of claim 2, wherein said solvent comprises a solvent species selected from the group consisting of hexane, heptane, octane, nonane, decane, toluene and xylene.

5. The method of claim 1, wherein the precursor material comprises at least one tethered amine tantalum complex of formula (I).

6. The method of claim 1, wherein the precursor material comprises at least one tethered amine tantalum complex of formula (II).

7. The method of claim 1, wherein the precursor material comprises at least one tantalum amide compound of formula (III).

8. The method of claim 1, wherein the tantalum- and nitrogen-containing precursor contains at least one silicon-containing group.

9. The method of claim 8, wherein the silicon-containing group is selected from the group consisting of silyl, alkylsilyl and alkyl(alkylsilyl)silyl.

10. The method of claim 1, wherein said contacting comprises ALD or CVD.

11. The method of claim 1, wherein said volatilization and contacting comprises liquid delivery vapor deposition.

12. The method of claim 1, wherein said substrate comprises a microelectronic device structure.

13. The method of claim 12, wherein said microelectronic device structure comprises integrated circuitry.

14. The method of claim 13, wherein said integrated circuitry includes copper metallization and/or ferroelectric layers.

15. The method of claim 13, wherein said integrated circuitry includes copper metallization.

16. The method of claim 13, wherein said integrated circuitry comprises at least one ferroelectric layer.

17. The method of claim 1, wherein the tantalum- and nitrogen-containing precursor comprises $\eta^2$-N,N'-dimethylethylenediamino-tris-dimethylaminotantalum (DEMAT).

18. The method of claim 1, wherein the tantalum- and nitrogen-containing precursor comprises bis-diethylamino-tris-dimethylaminotantalum.

19. The method of claim 1, wherein the tantalum- and nitrogen-containing precursor comprises diethylethylenediamino-tris-dimethylaminotantalum.

20. The method of claim 1, wherein the tantalum- and nitrogen-containing precursor comprises $\eta^2$-N,N'-dimethylpropanediamino-tris-dimethylaminotantalum.

* * * * *

UNITED STATES PATENT AND TRADEMARK OFFICE
CERTIFICATE OF CORRECTION

PATENT NO.       : 7,838,073 B2                                Page 1 of 1
APPLICATION NO.  : 12/773650
DATED            : November 23, 2010
INVENTOR(S)      : Tianniu Chen It is certified that error appears in the above-identified patent and that said Letters Patent is hereby corrected as shown below:

Column 5, line 63, "$NR^B$" should be -- $NR^8$ --.

Column 7, line 42, "silylene $C_1$-$C_4$" should be -- silylene (–$SiH_2$–) $C_1$-$C_4$ --.

Signed and Sealed this
Eighth Day of March, 2011

David J. Kappos
*Director of the United States Patent and Trademark Office*